United States Patent

Heuer et al.

[11] Patent Number: 5,672,568
[45] Date of Patent: Sep. 30, 1997

[54] ROOT GROWTH INHIBITORS FOR BUILDING MATERIALS COMPRISING MONOHYDRIC ALCOHOL ESTERS OF MECOPROP

[75] Inventors: Lutz Heuer; Heinz-Joachim Rother, both of Krefeld, Germany

[73] Assignee: Bayer Aktiengesellschaft, Leverkusen, Germany

[21] Appl. No.: 605,087

[22] PCT Filed: Aug. 19, 1994

[86] PCT No.: PCT/EP94/02768

§ 371 Date: Feb. 28, 1996

§ 102(e) Date: Feb. 28, 1996

[87] PCT Pub. No.: WO95/06408

PCT Pub. Date: Mar. 9, 1995

[30] Foreign Application Priority Data

Sep. 1, 1993 [DE] Germany .......................... 43 29 419.7

[51] Int. Cl.⁶ .................................................. A01N 39/02
[52] U.S. Cl. .................. 504/317; 71/DIG. 1; 52/741.3; 428/540; 428/541; 428/907; 428/911

[58] Field of Search ..................... 504/317; 428/540, 428/541, 907, 911; 52/741.3

[56] References Cited

U.S. PATENT DOCUMENTS 3,231,398  1/1966  Pauli et al. ................... 106/16
5,116,414  5/1992  Burton et al. ................ 71/121

FOREIGN PATENT DOCUMENTS 825875  12/1959  United Kingdom.

*Primary Examiner*—S. Mark Clardy
*Attorney, Agent, or Firm*—Sprung Horn Kramer & Woods

[57] ABSTRACT

There is described the use of compounds of the formula (II)

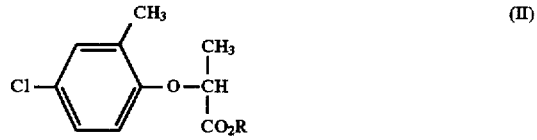

in which R has the meaning given in the description, as root penetration inhibitors.

2 Claims, No Drawings

ROOT GROWTH INHIBITORS FOR BUILDING MATERIALS COMPRISING MONOHYDRIC ALCOHOL ESTERS OF MECOPROP

This application has been filed under 35 USC 371 as a national Stage application of PCT/EP94/02768, filed Aug. 19, 1994.

The present invention relates to the use of 2-methyl-4-chlorophenoxypropionic ester for preventing roots from growing into and through buildings, building materials and insulating compounds, and to root-resistant bitumen mixtures, jointing compounds and insulations.

In building materials, root penetration results in undesirable damage to the material. Plant roots can destroy, in particular, plastic materials, such as sealing compounds, sheeting for roofs, but also asphalt. The penetration of roots into seals of channels and drain channels, coverings of flat roofs, in bitumen insulation of pipelines, bridge buildings and hydraulic structures, and the growth of roots into and through light bitumen roads are generally known problems. Leakages, corrosion and damage to buildings, roads and pipelines may result.

The addition of anti-root active compounds to building materials is known and described, for example, in F. Hegemann, Abiogene Bitumenadditive, [Abiogenic Bitumen Additives], Bitumen-Teere-Asphalte-Peche 24, 105 (1973).

It is furthermore known that herbicides such as, for example, 2,4-dichlorophenoxyacetic acid, 2,4,5-trichlorophenoxyacetic acid and α-naphthylacetic acid, or their salts, amides or esters, for example isooctyl ester or 1-hydroxy-2-butoxyethane ester, and furthermore phenyl-N-isopropylcarbaminate and p-chlorophenyldimethylurea can be used as root penetration inhibitors (DE 1 108 833).

There are also described mixtures of condensation products of monochloroacetic acid with various o-chlorophenols or o-chlorocresols, which are said to feature these characteristics (see DE 1 109 294).

Finally, it is known that esters of glycols or higher polyols with MCPP acid (2-methyl-4-chlorophenoxypropionic acid) have a root-inhibitory action (DE 1 196 115). However, the same application shows that the activity of esters of MCPP acid with monoalcohols is considerably lower than the activity of such esters with polyglycols.

Surprisingly, it has now been found that, in contrast to the teaching of DE 1 196 115, it is precisely those esters of MCPP acid which are prepared from the monoalcohols of the general formula (I)

R—OH  (I)

in which

R represents Me, Et, Pr, $^i$Pr, $^{n,i,s,t}$-Bu, $^{n,i,neo,t}$-pentyl, $^n$-hexyl, $^n$-heptyl, $^n$-octyl, 2-ethylhexyl, $^n$-nonyl, $^n$-decyl, $^n$-undecyl, $^n$-dodecyl, $^n$-tetradecyl, $^n$-tridecyl, $^n$-pentadecyl, $^n$-octadecyl, $^n$nonadecyl, $^n$-eicosyl or their branched structural isomers, or R is interrupted by one or more oxygen atoms, such as, for example, —CH$_2$—CH$_2$—OR$^1$,

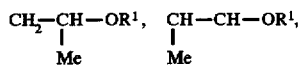

i.e. monoether alcohols of ethylene glycol, such as, preferably, 2-(n-butoxy)ethyl or propylene glycol, the latter with its structural isomers, where R$^1$ represents H or is defined as R, with the proviso that R$^1$ is repeated not more than 10 times, have a very good activity as root penetration inhibitors.

In the case of the branched structural isomers, those alkyl radicals which can be prepared by means of a Grubert reaction, such as, for example, 2-hexyldecanol (Isofol 16), 2-butyloctanol (Isofol 12), 2-decyltetradecanol (Isofol 24), 2-octyldodecanol (Isofol 20) and other Isofols (by Condea, Brunsbüttel) from 10 to 30, or mixtures of these, are particularly preferred.

Preferred amongst these esters are those of the alcohols of the formula (I)

in which

R represents C$_1$–C$_{10}$-alkyl, CH$_2$—CH$_2$—OR$^1$,

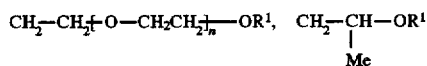

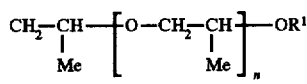

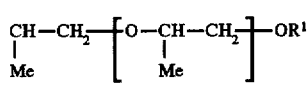

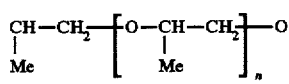

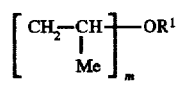

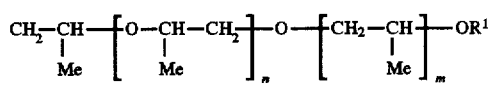

where

R$^1$ represents H, Me, Et, Pr, Bu, pentyl, hexyl, heptyl, octyl, n represents 0 to 8 and m represents 0 to 8.

All MCPP acid ester isomers and racemic and optically active MCPP acid esters are used according to the invention. The esters can be used singly or in combination with each other. For the purpose of root-resistant treatment, the esters are mixed the building materials or insulating compounds directly in the form of solution or other preparations such as, for example, with bitumen, various types of tar pitch. Exemplary and preferred jointing compounds are described, for example, in WO 92/10537.

The customary use concentration of the MCPP acid esters are 0.2 to 5% by weight based on bitumen.

The esters can be prepared by known methods (see, for example, Organikum [Laboratory Practical in Organic Chemistry], Deutscher Verlag der Wissenschaften 1990, pp. 373, 388, 405, 408, 389, 402, 403, 173, 199, 388, 404) and can generally be obtained in pure form by distillation, rectification or distillation using a bulb tube. If the esters cannot be distilled any longer, they are to be purified by chromatography on silica gel. The pure esters comprise less than 0.8% of MCPP acid.

The following esters were tested in accordance with DIN 4062 for their protective action against root penetration.

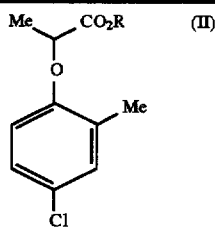

| R | Test for root penetration resistance in accordance with DIN 4062 | Refractive index boiling points |
|---|---|---|
| —Me | ≧0.8% no penetration | b.p.: 92–98/0.5 mm |
| -nC$_6$H$_{13}$ | ≧0.8% no penetration | $n_D^{25}$: 1.4945 |
| —CH$_2$—CH$_2$—O—Bu | ≧0.5% no penetration | $n_D^{25}$: 1.4928 |
| -n-C$_8$H$_{17}$ | ≧0.8% no penetration | $n_D^{25}$: 1.4895 |
| —(CH$_2$—CH$_2$—O)$_3$Me | | b.p.: 163/0.1 |
| -$n$C$_{10}$H$_{21}$ | ≧0.8% no penetration | $n_D^{25}$: 1.4900 |
| —(CH$_2$—CH$_2$O)$_3$—Et | | b.p.: 163/0.15 |
| —(CH$_2$—CH$_2$O)$_3$—Bu | | b.p.: 170/0.15 |
| —CH$_2$—CH—Bu<br>   \|<br>   C$_2$H$_5$ | ≧0.5% no penetration | $n_D^{25}$: 1.4903 |
| 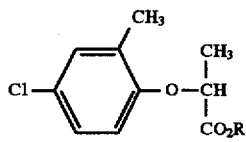 | | b.p.: 125/0.2 |
| Dipropylene glycol methyl ether | | b.p.: 138/0.2 |
| Tripropylene glycol methyl ether | | b.p.: 163/0.07 |
| Comparison tests | | |
| R—O—CH$_2$CH$_2$—OR | ≧0.8% no penetration | b.p.: 213/0.1 |
| R—O—(CH$_2$CH$_2$)$_Q$—OR | ≧0.8% no penetration | |
| R—O—(CH$_2$CH$_2$)$_Q$—OR | ≧0.8% no penetration | |

Q = 1 to 10, mean molecular weight ~ 200

In accordance with DIN 4062, esters of monoalcohols therefore do not perform less well with regard to their activity than esters of di- or polyalcohols, but, in contrast to the polyglycol diol diesters, are easier to handle from a technical point of view due to their chemicophysical properties. Since, moreover, the monoesters comprise less MCPP acid based on the molecular weight than the diesters, they are superior to the diesters with regard to their activity per ester group.

We claim:

1. A building material or insulating composition carrying a root penetration-protecting amount of a 2-methyl-4-chlorophenoxypropionic monoester of the formula

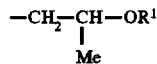

(II)

in which

R represents Me, Et, Pr, $^i$Pr, $^{n,i,s,t}$-Bu, $^{n,i,neo,t}$-pentyl, $^n$-hexyl, $^n$-heptyl, $^n$-octyl, 2-ethylhexyl, $_n$-nonyl, $^n$-decyl, or their branched structural isomers, or R is —CH$_2$—CH$_2$—OR$^1$, —CH$_2$—CH—OR$^1$
       \|
       Me or —CH$_2$—CH—OR$^1$.
       \|
       Me 2. A method for protecting buildings, building materials and insulating compositions against penetration by the roots of vegetation, which comprises applying thereto an amount effective therefor of a 2-methyl-4-chlorophenoxypropionic monoester of the formula

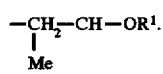

(II)

in which

R represents C$_{1-C10}$-alkyl, CH$_2$—CH$_2$—OR$^1$,

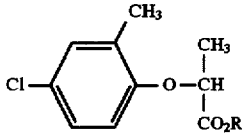

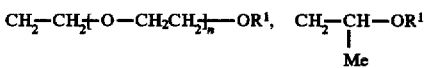

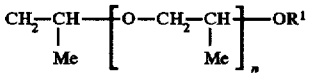

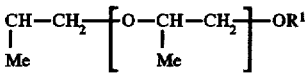

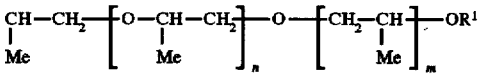

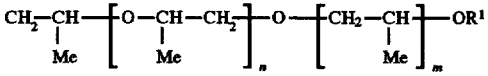

where

R$^1$ represents H, or C$_1$–C$_8$-alky and n and m independently represent 0 to 8.

* * * * *